United States Patent [19]

Lattin et al.

[11] 4,271,840
[45] Jun. 9, 1981

[54] RESERVOIR SYSTEM FOR A BODY IMPLANTABLE MEMBER

[75] Inventors: Gary A. Lattin, Coon Rapids; Paul D. Sorenson, Blaine, both of Minn.

[73] Assignee: Medtronic, Inc., Minneapolis, Minn.

[21] Appl. No.: 76,401

[22] Filed: Sep. 17, 1979

[51] Int. Cl.³ .............................................. A61N 1/00
[52] U.S. Cl. .................................. 128/1 R; 128/419 P
[58] Field of Search .................... 128/419 P, 784–786, 128/348, 213, 260, 1 R

[56] References Cited

U.S. PATENT DOCUMENTS

| | | | |
|---|---|---|---|
| 3,703,174 | 11/1972 | Smith | 128/348 |
| 3,913,587 | 10/1975 | Newash | 128/419 P |
| 4,094,321 | 6/1978 | Muto | 128/419 |

Primary Examiner—William E. Kamm

Attorney, Agent, or Firm—Schroeder, Siegfried, Ryan, Vidas, Steffey & Arrett

[57] ABSTRACT

A reservoir system for a flexible, elongated, body implantable member of the type that is adapted to provide communication between separated body sites. A reservoir body is formed of a cup and cover which cooperate to define a cavity. Slots in the cup and/or cover admit a portion of the elongated member into the cavity. A tool is engageable with an elongated member portion within the cavity to coil a desired length of the elongated member within the cavity. On growth of the body, the coil is uncoiled to accommodate the greater distance between the body sites between which the elongated member extends. In a preferred embodiment, the tool is first rotated in one direction to coil a desired length of the elongated member within the cavity and then rotated in the other direction to uncoil and recoil all but a portion of the outermost coil spiral.

19 Claims, 9 Drawing Figures

RESERVOIR SYSTEM FOR A BODY IMPLANTABLE MEMBER

DESCRIPTION

Background of Prior Art

The use of elongated body implantable members for communication between separated body sites is known in the prior art. For example, catheters have long been used to provide a passageway for fluids within the body. Also, electrical leads for the delivery of stimulation energy have many applications. Such elongated members are often implanted on a permanent or, at least, long-term basis.

The rapid growth rates of infants and young children poses a problem when it is necessary to establish a communication between separated body sites. That is, with growth, the distance between the separated sites can increase significantly. Thus, a member that is the proper length at the time of implant may become too short as the body grows. Because of the increased potential for complications from multiple surgical procedures, successive implants of increasing length is, at best, an undesirable resolution of the problem.

An implant that is too long at the time of implant is undesirable in that the extra length may entwine itself around a portion of the body. Thus, an implant having extra length to accommodate growth is not acceptable. Indeed, the standard lengths of many implants, electrical leads, for example, may be too long for some applications requiring that the extra length be taken up in some manner.

One approach to the above-noted pediatric implant problem, in the context of a cardiac pacemaker, is shown in U.S. Pat. No. 3,598,128 issued Aug. 10, 1971, in the name of William M. Chardack for LEAD STORING PACER. In accordance with the Chardack teachings, a groove is provided around the periphery of the pacemaker to receive an extra length of lead. The pacemaker is implanted within a pocket in a manner known in the prior art. As the body grows, a force is imparted to the lead which causes the pocketed pacemaker to revolve, thus releasing the extra lead from the groove, as needed. Another approach, again in the context of a cardiac pacemaker, is disclosed in U.S. Pat. No. 4,013,081 issued Mar. 22, 1977, to Steve A. Kolenik for PEDIATRIC CARDIAC PACER SYSTEM. The Kolenik system employs a bag around a portion of the periphery of its pulse generator with the lead being loosely contained within the bag. On growth of the body, the lead tightens around the pulse generator body to allow a greater lead extension. Still another known approach to the pediatric implant problem has been employed as an improvement to the classic procedure for draining off excess fluid from the brain to help infants with hydrocephalus. A shunt, in the form of a catheter, has its tip positioned in one of the fluid filled cavities of the brain and drains fluid from the head into the heart or abdomen where it is re-absorbed into the blood stream. In the improvement to this procedure, an extra length of the catheter is contained within a Silastic pouch, in coils, the pouch being positioned in the chest. As the patient grows, there is a progressive uncoiling of the catheter. It is standard procedure to "wrap" excessive lead lengths around the pulse generator body during pacemaker implants.

The pacemaker systems described above require that the extra lead be taken up at and provided from the site of the pacemaker and, in one instance, require a rotational movement of the pacemaker within the body as additional lead is provided. Further, the continuing effort to decrease the size of pulse generator units severely limits the amount of "extra" lead that these systems can accommodate. Indeed, and with particular reference to the Kolenik system, such systems may contribute to the overall dimensions of the implantable unit which is counter to the efforts expended toward a size reduction.

BRIEF SUMMARY OF INVENTION

The present invention provides a system for containing a flexible, elongated, body implantable member that is adapted to provide communication between separated body sites. In a preferred embodiment, a cavity is defined by cooperating cup and cover means. At least one of the cup and cover means are provided with slot means for admitting a portion of the elongated member into the cavity. An aperture allows admittance of a tool into the cavity, the tool engaging the elongated member portion within the cavity for coiling of the member within the cavity. After coiling, the aperture may be closed by a plug. The system may be employed to store excess member length or to provide extra member length as required by body growth. In a preferred embodiment for the latter application, the tool is rotated in one direction until the desired length of the elongated member is coiled within the cavity. The tool is then rotated in the other direction to uncoil and recoil all but a portion of the outermost spiral of the first formed coil. Thus contained, the member may be withdrawn in either direction.

DETAILED DESCRIPTION OF INVENTION

Figure 1:
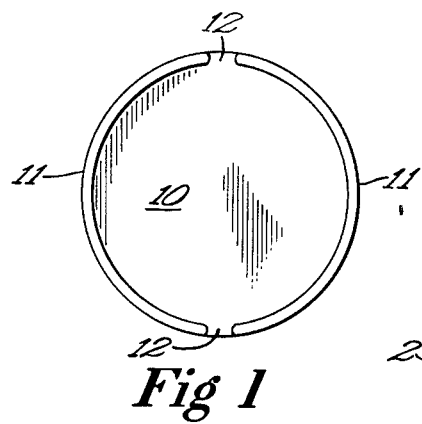
FIG. 1 is a top view of an element forming a portion of a preferred embodiment of the present invention.
Figure 2:
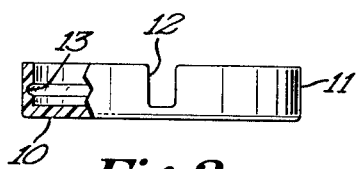
FIG. 2 is a side view and partial cutaway of the element of FIG. 1.

Referring now to FIGS. 1 and 2, there is shown a top and side view, respectively, of an element forming a portion of a preferred embodiment of the present invention. Specifically, FIGS. 1 and 2 show a cup-shaped element formed of a main wall 10 and a sidewall 11, the sidewall 11 being provided with slots 12 disposed at substantially 180° relative to each other. The inner face of the sidewall 11 is provided with a groove 13 whose function will be described more fully below.

Figure 3:
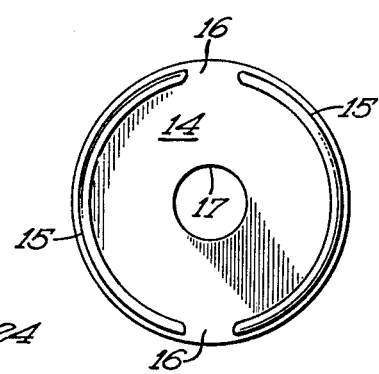
FIG. 3 is a bottom view of an element forming a portion of a preferred embodiment of the present invention.
Figure 4:
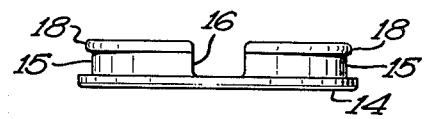
FIG. 4 is a side view of the element of FIG. 3.

Referring now to FIGS. 3 and 4, there is shown a bottom and side view, respectively, of a cover which cooperates with the cup of FIGS. 1 and 2 to define a cavity. Specifically, the cover of FIGS. 3 and 4 is formed of a main wall 14 and a sidewall 15, the sidewall 15 having opposing slots 16. The slots 16 are slightly larger than the slots 12 and are disposed at substantially 180° relative to each other. The termini of the sidewalls 15 are provided with an extending lip 18, the lip 18 being adapted to cooperate with the groove 13 to assist in maintaining the cup and cover in an assembled configuration. The main wall 14 is provided with a central bore 17 whose function will be described more fully below.

Figure 5:
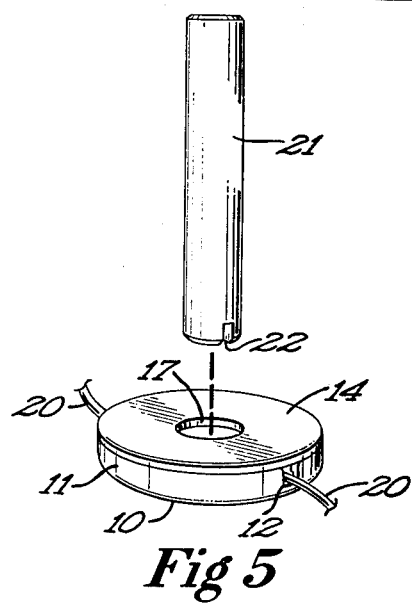
FIG. 5 is a view illustrating the cooperation of the elements forming a preferred embodiment of the present invention.

FIG. 5 illustrates the cup and cover of FIGS. 1-4 in assembled relation to define a generally cylindrical cavity between the main walls 10 and 14 and within the sidewalls 11 and 15. That generally cylindrical cavity is intended to contain a flexible, elongated, body implantable member 20. Before assembling the cup and cover, a portion of the elongated member 20 is positioned within the cavity as by placing it along the main wall 10 extending from one of slots 12 to the other. Slots 16 are then generally aligned with the slots 12, with the sidewall 15 within the sidewall 11, and the cup and cover are then urged toward each other until the lip 18 engages the groove 13. At this point, main wall 14 abuts against the terminus of sidewall 11.

The slots 12 are preferably of a size approximating the cross-sectional diameter of the elongated member 20 so as to prevent the member 20 from easily slipping out of the cavity defined by the cup and cover. However, the relationship between the size of the slot 12 and elongated member 20 should be such that only a small force is necessary to move the elongated member 20 through the slot 12. Slots 16 are larger than slots 12 to remove any criticality in alignment between the slots 16 and the slots 12 when the cup and cover are assembled. Body fluids provide a lubrication effect after implant.

An elongated tool 21 is provided with a notch 22 at one end thereof. The tool has a cross-section such that it will easily pass through the aperture 17 to engage, via notch 22, elongated member 20 within the cavity formed by the cup and cover. With the elongated member 20 within the notch 22, rotation of the tool 21 will cause the elongated member 20 to coil within the cavity.

Figure 6:
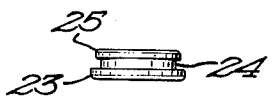
FIG. 6 illustrates an element forming a portion of a preferred embodiment of the present invention.

On removal of the tool 21 from the cavity, a plug may be employed to cover the aperture 17 for implant. Such a plug is illustrated in FIG. 6 and includes a plate 23 whose dimensions are larger than that of aperture 17, a post 24 configured to fit within the aperture 17 and a lip 25 adapted to engage the inner surface of main wall 14 to maintain the plug in position, all in known manner. The cup, cover and plug may be of any biocompatible material whose properties will serve to maintain the configuration illustrated and discussed herein.

Figure 7:
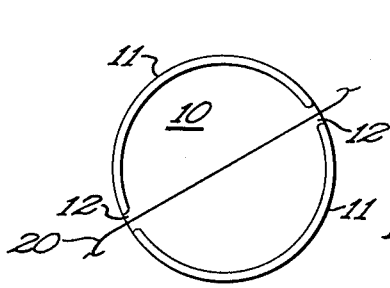
FIGS. 7-9 illustrate the positioning of an elongated member within a preferred embodiment of the present invention and the configuration of such a member as stored within the reservoir system of the present invention.
Figure 8:
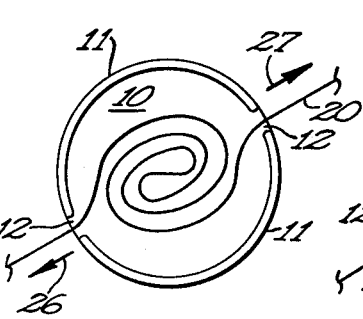

FIG. 7 is a top view of an elongated member 20 extending between the slots 12 and along the main wall 10 of the cup of FIGS. 1 and 2. With the cup and cover fully assembled, the tool 21 is inserted into the cavity, via aperture 17, and into engagement with the elongated member 20 therein. Rotation of the tool 21 will then result in a coiling of member 20 within the cavity. Such a coil resulting from a clockwise rotation of the tool 21 is illustrated in FIG. 8 with the cover removed for the sake of clarity. With the elongated member 20 coiled as illustrated in FIG. 8, a force acting along the direction of the arrows 26 and 27 will cause the elongated member to uncoil thereby providing an extra length of the elongated member to accommodate a greater distance between the body sites between which the elongated member 20 extends. Generally, with the coil configuration of FIG. 8, a force in the direction of both of the arrows 26 and 27 will be necessary to provide a reliable uncoiling of the elongated member 20. The coil configuration of FIG. 8 is suitable when the system of the present invention is employed as a reservoir to provide additional length to accommodate growth when the system is placed in a pocket generally at or toward the midpoint between the sites to which the elongated member 20 extends.

Figure 9:
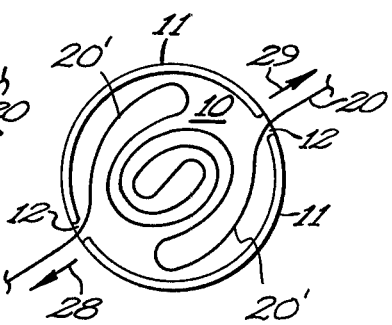

In some instances, it may be necessary or desirable to place a reservoir system in accordance with the present invention at or reasonably adjacent one of the body sites between which elongated member extends. In that instance, a reliable uncoiling of the elongated member 20 within the cavity may be accomplished by first coiling the desired length of the elongated member 20 within the cavity by rotating the tool 21 in a first direction. The tool may then be rotated in the other direction causing at least the central portion of the coil within the cavity to uncoil and recoil. Preferably, rotation of the tool 21 is continued until all but a portion of the outermost spiral 20' (See FIG. 9) has been uncoiled and recoiled. In the configuration illustrated in FIG. 9, a force in the direction of either of the arrows 28 and 29 will cause a reliable withdrawal of the elongated member 20 from the associated slot 12.

Obviously, many modifications and variations of the present invention are possible in light of the above teachings. For example, the elements, or at least the cover member, may be made of a material sufficiently transparent to allow the easy viewing of the state of the coil within the cavity. Other tool configurations which are capable of engaging the elongated member within the cavity for coiling the same therein may be employed without departing from the scope of the present invention. Also, the reservoir system of the present invention may be employed with catheters, electrical leads and other flexible, elongated, body implantable members. It is therefore to be understood that, within the scope of the appended claims, the invention may be practiced otherwise than as specifically described.

We claim:

1. A container system for a flexible, elongated, body implantable member of the type which is adapted to provide communication between separated body sites which comprises body means having a cavity for accepting a portion of such member therein and tool means insertable within said cavity and engageable with a member portion therein for coiling such member within said cavity on rotation of said tool means.

2. The system of claim 1 wherein said tool means further comprises means for sequentially uncoiling and recoiling at least the inner portion of a previously coiled member portion within said cavity.

3. The system of claim 1 wherein said tool means comprises notched means engageable with a member portion within said cavity.

4. The system of claim 1 wherein said body means comprises cup means and cover means cooperating to define said cavity.

5. The system of claim 4 wherein at least one of said cup and cover means are provided with slot means for admitting a member portion into said cavity.

6. The system of claim 5 wherein said cavity is generally cylindrical, said slot means comprising first and second slot means angularly disposed at substantially 180° relative to each other.

7. The system of claim 6 wherein said body means is provided with aperture means for admittance of said tool means into said cavity.

8. The system of claim 7 further comprising plug means for closing said aperture means.

9. The system of claim 8 wherein said tool means comprises notched means insertable through said aperture means and engageable with a member portion within said cavity.

10. A container system for a body implantable electrical lead, the lead being adapted to provide electrical communication between separated body sites, which comprises:
 body means formed of cup means and cover means cooperating to define a cavity;
 slot means within at least one of said cup means and cover means for admitting a portion of a lead into said cavity; and
 tool means engageable with a lead portion within said cavity and rotatable in a first direction for coiling such lead within said cavity, such lead being uncoiled to accommodate the greater distance between said body sites on growth of the body.

11. The system of claim 10 wherein said tool means further comprises means rotatable in the other direction for uncoiling and recoiling at least the inner portion of a coiled lead within said cavity.

12. The system of claim 10 wherein said cavity is generally cylindrical, said slot means comprising first and second slot means angularly disposed at substantially 180° relative to each other.

13. The system of claim 12 wherein said body means is provided with aperture means for admittance of said tool means into said cavity.

14. The system of claim 13 further comprising plug means for closing said aperture means.

15. The system of claim 14 wherein said tool means comprises notched means insertable through said aperture means and engageable with a member portion within said cavity.

16. The system of claim 10 wherein said tool means comprises notched means engageable with said member portion within said cavity.

17. A method of storing an extra length of a flexible, elongated, body implantable member for release as required by the growth of the body, comprising the steps of:
 forming a body part including a cavity and first and second slots;
 positioning said member in said slots and through said cavity;
 engaging said member within said cavity with a tool;
 rotating said tool to coil a desired length of said member in said cavity.

18. The method of claim 17 wherein the step of rotating comprises the steps of:
 rotating said tool in one direction to form a first coil in said member; and
 rotating said tool in the other direction to uncoil and recoil the inner portion of said first coil.

19. The method of claim 18 wherein the second rotating step comprises the step of rotating said tool in said other direction to uncoil and recoil all but a portion of the outermost spiral of said first coil.

* * * * *